United States Patent [19]

Bergthaller

[11] Patent Number: 5,463,072
[45] Date of Patent: Oct. 31, 1995

[54] PROCESS FOR THE PREPARATION OF NAPHTHOLIC 2-EQUIVALENT CYAN COUPLERS

[75] Inventor: Peter Bergthaller, Bergisch Gladbach, Germany

[73] Assignee: Agfa Gevart AG, D-51368, Leverkusen, Germany

[21] Appl. No.: 64,466

[22] Filed: May 21, 1993

[30] Foreign Application Priority Data

Jun. 3, 1992 [DE] Germany .................. 42 18 308.1

[51] Int. Cl.$^6$ .................. C07D 249/06; C07D 249/08; C07D 409/04; C07D 401/04
[52] U.S. Cl. .................. 548/255; 548/146; 548/266.2; 548/267.8; 548/260; 546/168; 546/167
[58] Field of Search .................. 546/167, 168; 548/255, 146, 266.2, 267.8, 260

[56] References Cited

U.S. PATENT DOCUMENTS

| | | | |
|---|---|---|---|
| Re. 29,379 | 8/1977 | Shiba et al. | |
| 3,617,291 | 11/1971 | Sawdey | 96/100 |
| 3,733,201 | 5/1973 | Barr | 96/100 |
| 3,933,500 | 1/1976 | Shiba et al. | 96/74 |
| 4,477,563 | 10/1984 | Ichijima et al. | 430/544 |
| 5,021,331 | 6/1991 | Vetter et al. | 430/544 |

FOREIGN PATENT DOCUMENTS

| | | |
|---|---|---|
| 0401612 | 12/1990 | European Pat. Off. |
| 2222674 | 10/1974 | France . |
| 1800420 | 5/1969 | Germany . |
| 3209486 | 9/1982 | Germany . |

*Primary Examiner*—David B. Springer
*Attorney, Agent, or Firm*—Connolly & Hotz

[57] ABSTRACT

Compounds of formula I

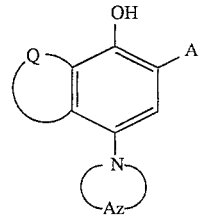

wherein
A denotes a group having an electron acceptor character;
Az denotes a group for completing a 5-membered heteroaromatic ring (azole ring) to which a 5- or 6-membered carbocyclic or heterocyclic ring may be attached by condensation and
Q denotes a group for completing a condensed benzene or pyridine ring
are prepared by oxidizing a compound of formula II

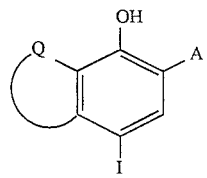

wherein
A and Q have the meanings indicated
with an oxidizing agent which transfers acyloxy groups and then reacting the product with a compound of formula III

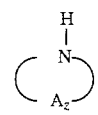

wherein
Az has the meaning indicated.

12 Claims, No Drawings

PROCESS FOR THE PREPARATION OF NAPHTHOLIC 2-EQUIVALENT CYAN COUPLERS

This invention relates to a process for the preparation of 2-equivalent couplers. The invention relates in particular to a process for the preparation of compounds of formula I which are suitable as 2-equivalent couplers

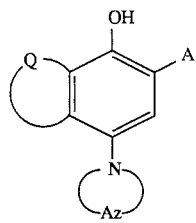

in which formula,

A denotes a group having an electron acceptor character, e.g. carbamoyl, sulphamoyl or acylamino;

Az denotes a group for completing a 5-membered heteroaromatic ring (azole ring) to which a 5- or 6-membered carbocyclic or heterocyclic ring may be attached by condensation, and Q denotes a group for completing a condensed benzene or pyridine ring.

2-Equivalent couplers have acquired great technical importance in the production of colour photographic materials for various reasons. They provide a saving in silver halide due to a reduced requirement of oxidation equivalents, they enable optimum coupling kinetics to be established by choice of the fugitive group, they couple in many cases with greater uniformity to the desired azomethine or indophenol dyes so that images with purer colours can be produced and the fugitive group released in the coupling reaction, which may have development activating or development inhibiting properties, provides the possibility of an additional control of the development process, e.g. by so-called interimage or edge effects.

Among the fugitive groups, heterocyclic fugitive groups having one or more N atoms as nucleophilic centres are particularly important, especially the monocyclic or bicyclic triazoles. The introduction of heterocyclic azoles into yellow coupler structures from the series of acylacetanilides is conventionally carried out by a reaction of the halogenated couplers with the fugitive group by a nucleophilic substitution.

In the known and technically used classes of cyan couplers, the phenols and naphthols, the replacement of halogen by heterocyclic fugitive group nucleophils having an N atom is not possible according to the state of the art because the halogen atom is highly stabilized by the aromatic system.

Heterocyclic azoles may to a limited extent be introduced into naphthols by ring synthetic measures, e.g. by 1,3-dipolar cycloadditions or, as in the case of benzo-triazoles, triazoles, by a modification of azo dye structures. An improved process for the introduction of benzotriazoles into the coupling position of naphtholic cyan couplers has only recently become known (Angewandte Chemie 103/12 (1991) pages 1742–3). The process is based on the use of selenium compounds as polarity reversing reactants, preferably in the tetravalent form, which react with the couplers by a reaction similar to a Friedel-Crafts synthesis and the reaction products of which can be converted into 2-equivalent couplers. The driving power of the reaction appears to be the energetically favourable release of elementary selenium or tellurium.

One important objection to the use of Se(IV) compounds, e.g. selenium dioxide, ditosyl selenium diimine, dichloroselenium-N-tosylimine, selenium oxychloride or selenium tetrachloride, but also to the use of tellurium(IV) compounds as polarity reversing reagents for the nucleophilic coupling position is the high toxicity of these compounds, which is not reduced by incorporation in organic compounds and the resulting improved tissue tolerance but is in critical cases even increased. The use of Se(IV) and Te(IV) compounds is particularly contraindicated if after the end of the reaction the Se or Te is not completely precipitated as element, which would enable it to be removed.

There is therefore still a need for a technically uncomplicated method of synthesis of cyan couplers whereby a heterocyclic fugitive group can be subsequently incorporated in a 4-equivalent cyan coupler.

It was surprisingly found that simple reactions of naphtholic cyan couplers containing an iodine atom as fugitive group result in 2-equivalent couplers containing heterocyclic azole fugitive groups if they are converted by oxidation into hetero-iodinanes and reacted with heterocyclic azoles, preferably in the presence of bases.

The invention relates to a process for the preparation of a compound of Formula I

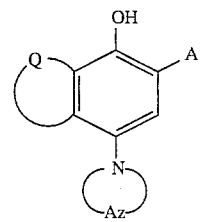

wherein.

A denotes a group having an electron acceptor character;

Az denotes a group for completing a 5-membered heteroaromatic ring (azole ring) to which a 5- or 6membered carbocyclic or heterocyclic ring may be attached by condensation, and Q denotes a group for completing a condensed benzene or pyridine ring, characterised in that a compound of formula II

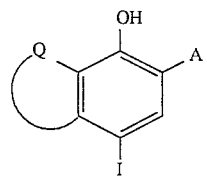

wherein

A and Q have the meanings indicated is oxidized with an oxidizing agent which transfers acyloxy groups and is then reacted with a compound of formula III

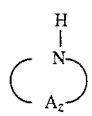

wherein

Az has the meaning indicated.

The group with electron acceptor character denoted by A may be, for example, a carbamoyl group, a sulphamoyl group or an acylamino group. The said groups may contain ballast groups, e.g. long chain alkyl groups and/or phenyl or phenoxy groups, which may be substituted, for example with alkyl, alkoxy, alkoxycarbonyl, alkylamino, acylamino, sulphonamido, carbamoyl and/or sulphamoyl groups.

A condensed benzene or pyridine ring completed by Q may be substituted, for example, by acylamino, sulphonamido, alkoxycarbonylamino, amino or hydroxyl groups.

The heteroaromatic ring completed by Az is in particular a 5-membered heteroaromatic ring containing at least 2, preferably not less than 3 nitrogen atoms (e.g. 1,2,3-triazole or 1,2,4-triazole) and optionally carrying a further condensed aromatic or heteroaromatic ring (e.g. benzotriazole).

Compounds of Formula II are known, e.g. from U.S. Pat. Nos. 3,642,485, 3,790,384 or DE-A-22 47 496. They may suitably be prepared from the corresponding 4-equivalent couplers by reaction with elementary iodine or with iodomonochloride, for which Friedel-Crafts catalysts are generally not required.

Suitable oxidizing agents for transferring acyloxy groups are in particular the higher valency acetates or tri-fluoroacetates of lead, thallium and manganese but also other oxidizing agents, e.g. the iodobenzene sulphonates or trifluoroacetates ("Kosers reagent", J. Org. Chem. 49 (1984), 4700; or "Zefirov's reagent" J. Org. Chem. 54 (1989), 2609). Chlorinating oxidizing agents are less suitable because they preferentially lead to chlorinated 2-equivalent couplers.

The compounds of Formula III which can be introduced as fugitive groups into naphtholic 4-equivalent couplers by the new process include, among the monocyclic heteroaromatic compounds, the imidazoles, 1,2,3-triazoles, 1,2,4-triazoles, tetrazoles and triazolones; and among the bicyclic compounds, the benzotriazoles, thienotriazoles, furotriazoles and tetrahydrobenzotriazoles.

In the compounds of Formula I, the group

is preferably a group of the formula

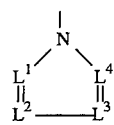

wherein two of the ring members ($L^1$, $L^2$, $L^3$, $L^4$) stand for a N atom and the two others stand for a group of the formula

wherein $R^1$ denotes H, alkyl, alkylthio, aryl, a heterocyclic group, (e.g. furan or thiazole) or $COOR^2$ ($R^2$=alkyl or aryl) and wherein the two $R^1$ groups may form a condensed benzene ring if $L^1$ and $L^2$ or $L^2$ and $L^3$ denote

The reaction of the heteroiodinanes obtained by oxidation from the compounds of Formula II with the compounds of Formula III is preferably carried out in solution in the presence of bases. Examples of suitable solvents for this purpose include dichloromethane, ethyl acetate, dioxane, tetrahydrofuran, 1,2-dimethoxymethane, chlorobenzene and pyridine.

Examples of suitable bases include strong organic bases of the amidine or guanidine series, e.g. tetramethylguanidine, diazabicyclononane or diazabicycloundecane but also peralkylated triamino-imino-phosphoranes.

The following are examples of compounds which may be prepared by the process according to the invention:

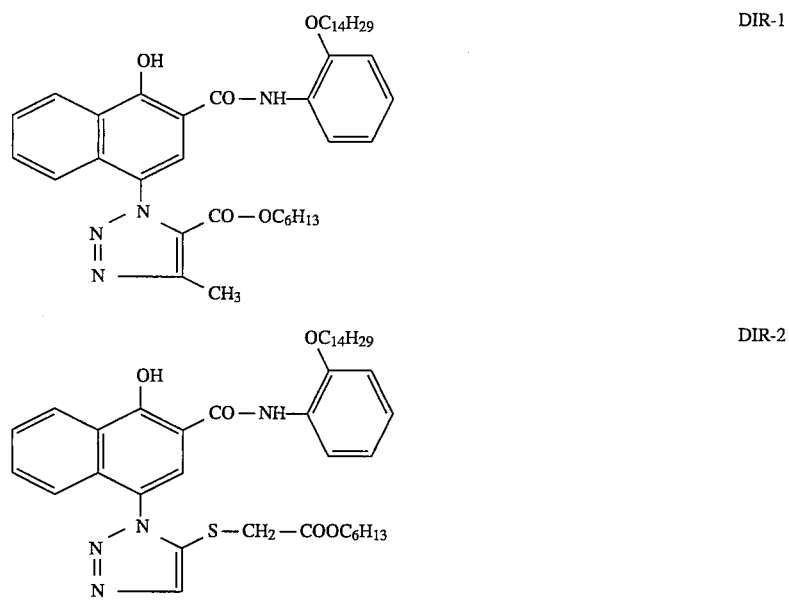

DIR-1

DIR-2

-continued
DIR-3
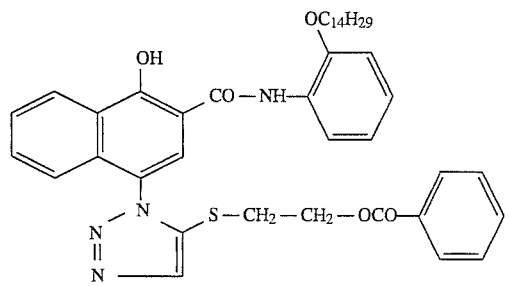
DIR-4
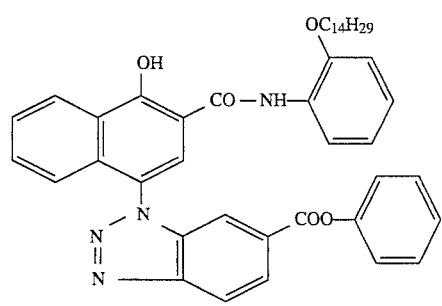
DIR-5
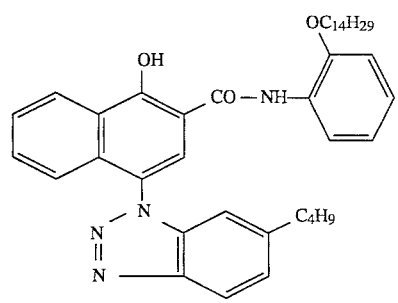
DIR-6
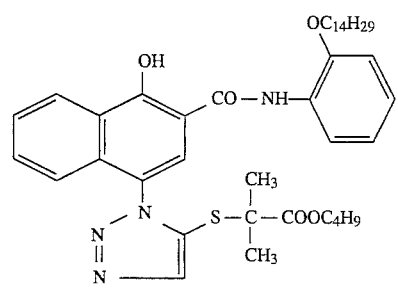
DIR-7
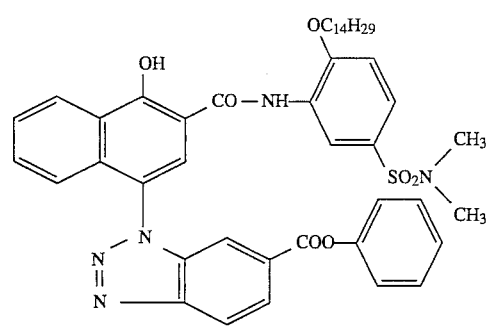

-continued
DIR-8
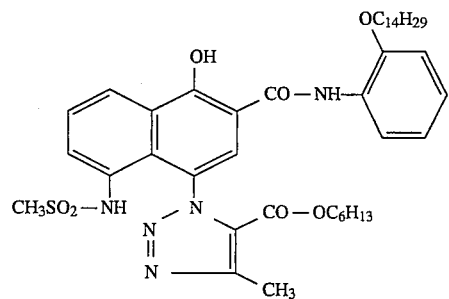
DIR-9
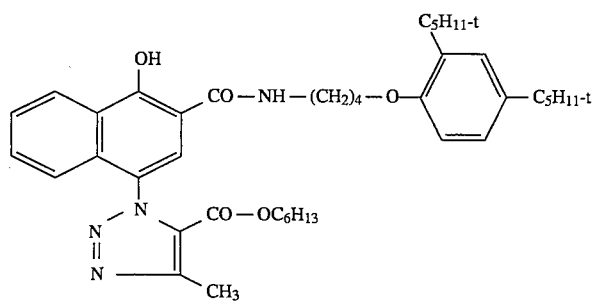
DIR-10
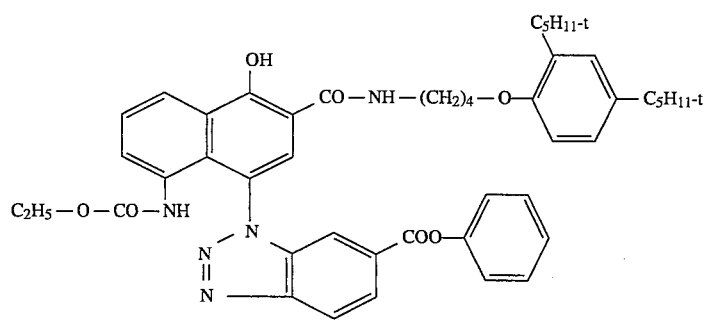
DIR-11
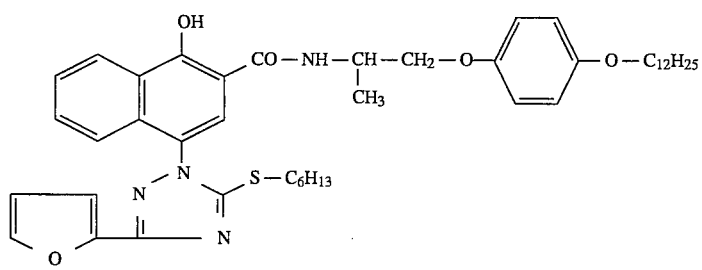
DIR-12
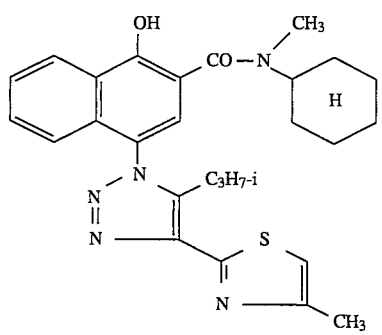

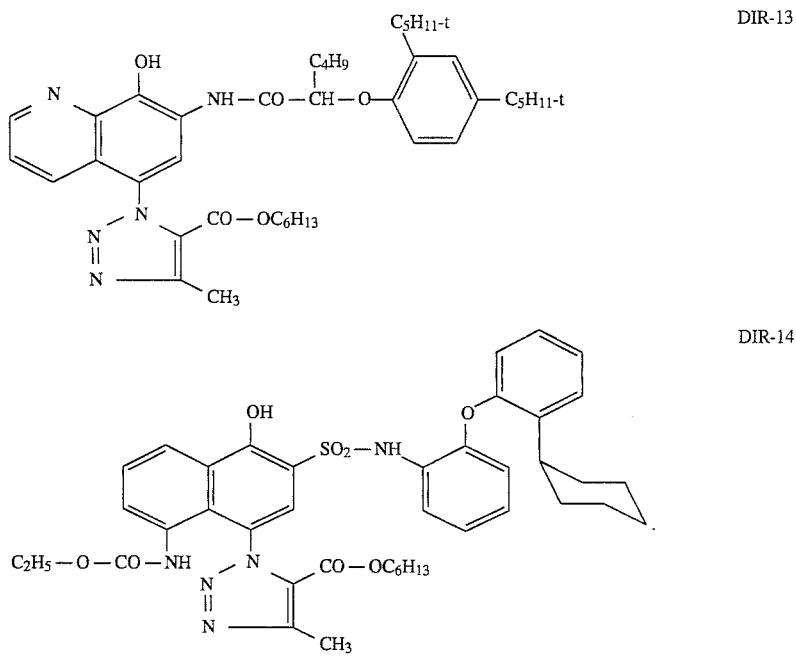

In the above formulae, the cyan-DIR couplers are shown with a bond between the coupling position of the coupler and one of the three N-atoms of the triazole ring. It is not claimed that this method of drawing the formulae correctly represents the true position. The triazole ring may also be attached to the coupling position by one of the two other N atoms or the compounds may be isomeric mixtures.

The process of the present invention is illustrated by the following example of a synthesis:

1.1 Compound DIR-1

4.75 g (10 mmol) of 1-naphthol-2-carboxylic acid-(2-tetradecyloxy)-anilide in 70 ml of pyridine are reacted with 2.6 g of iodine for 5 hours at room temperature with stirring. The iodised coupler crystallises when the solution is stirred into 200 ml of 10% hydrochloric acid. Yield: 4.4 g. Melting point: 72 to 74° C.

1.2 Compound DIR-1

3 g (5 mmol) of the iodised coupler from 1.1 are dissolved in 200 ml of dichloromethane and 1,55 g (5 mmol) of iodobenzene-bistrifluoroacetate are added with stirring. The mixture turns a dark colour. After it has been left to stand for over 1 hour and 1.2 g of 5-methyl-1,2,3-triazole-4-carboxyolic acid-n-hexyl ester and 1.2 g of tetramethylguanidine have been added, the solution is left to stand for 10 hours with exclusion of moisture. 20 ml of 10% hydrochloric acid are added, the phases are separated and the dichloromethane phase is washed with water. After dehydration over sodium sulphate, the organic phase is concentrated by evaporation, taken up in toluene and chromatographed with cyclohexane-toluene-ethyl acetate mixtures over 100 g of silica gel with increasing proportions of toluene and ethyl acetate.

After the removal of two spots which are obtained as first product, 1.2 g of compound DIR-1 melting at 82 to 84° C. (from cyclohexane) are obtained from the polar eluates.

$^1$H-NMR (200 Mhz, $CDC_3$, TMS) δ=14.03 (s, OH), 8.82 (s, NH), 8.18–8.22 (2d, CH), 8.04–8.08 (d, CH), 7.82 (s, CH), 7.6–7.77 (m, CH), 6.9–7.36 (m, CH) , 4.38–4.5 (t, $CH_2$) , 4.02–4.15 ( t, $CH_2$), 2.7–2.75 (s, $CH_3$), 1.9–1.97 (m, $CH_2$), 1.15–1.5 (m, $CH_2$, $CH_3$), 0.8–0.95 (m, $CH_3$)

The compounds of formula I which may be prepared by the process according to the invention are valuable 2-equivalent cyan couplers and in particular cyan DIR couplers, i.e. these compounds are capable of forming a cyan dye under chromogenic development and at the same time releasing a development inhibitor. Preferred examples of compounds prepared by the process according to the invention correspond to the general formula Ia

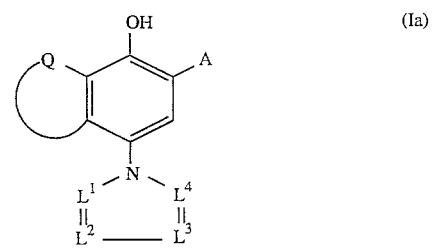

wherein A and Q have the meanings already indicated and 2 of the ring members ($L^1$, $L^2$, $L^3$, $L^4$) stand for a N atom and the two others stand for a group of the formula

wherein $R^1$ denotes alkyl, alkylthio aryl, a heterocyclic group (e.g. furan or thiazole) or —$COOR^2$ ($R^2$=alkyl or aryl). These compounds are new.

I claim:

1. A process for the preparation of a compound of formula I

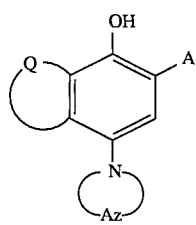

(I)

wherein
  A denotes a carbamoyl, sulphamoyl or acylamino group
  Az denotes a group for completing an azole ring to which a 5- or 6-membered carbocyclic ring may be attached by condensation, and
  Q denotes a group for completing a condensed benzene or pyridine ring,
characterized in that a compound of formula II

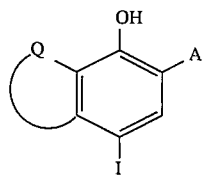

(II)

wherein
  A and Q have the meanings indicated,
is oxidized with an acyloxy group-transferring oxidizing agent selected from the group consisting of higher valency acetates and trifluoroacetates of lead, thallium and manganese, iodobenzene sulfonates and iodobenzene trifluoroacetates, and is then reacted with a compound of formula III

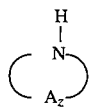

(III)

wherein
  Az has the meaning indicated.

2. A compound of formula Ia

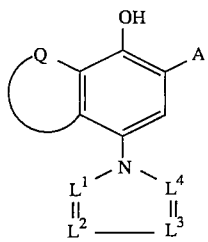

(Ia)

wherein
  A denotes a group having an electron acceptor character,
  denotes a group for completing a condensed benzene or pyridine ring, and
  $L^1$, $L^2$, $L^3$ and $L^4$ stand for ring members, two of the ring members being each a N atom and the two others each a group of the formula

wherein $R^1$ denotes alkyl, alkylthio, aryl, a furyl group, a thiazolyl group or $COOR^2$ ($R^2$=alkyl or aryl).

3. The compound of claim 2, wherein said compound has the formula

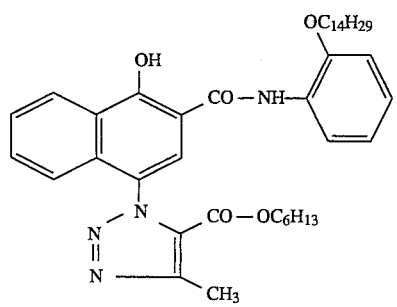

4. The compound of claim 2, wherein said compound has the formula

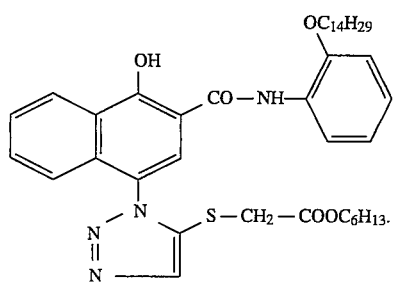

5. The compound of claim 2, wherein said compound has the formula

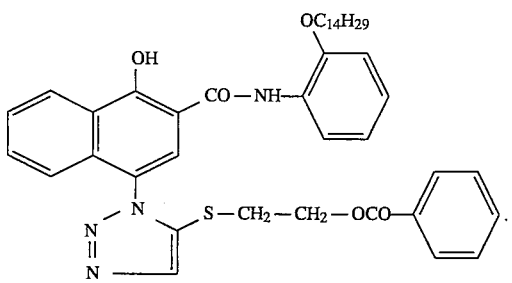

6. The compound of claim 2, wherein said compound has the formula

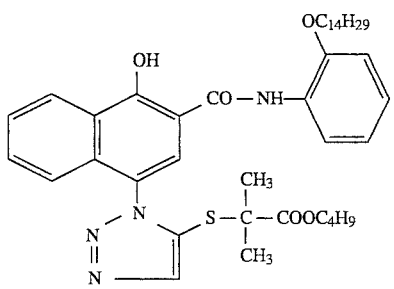

7. The compound of claim 2, wherein said compound has the formula

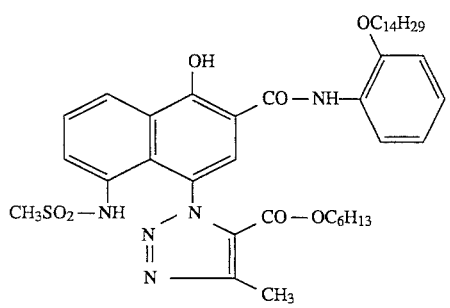

8. The compound of claim 2, wherein said compound has the formula

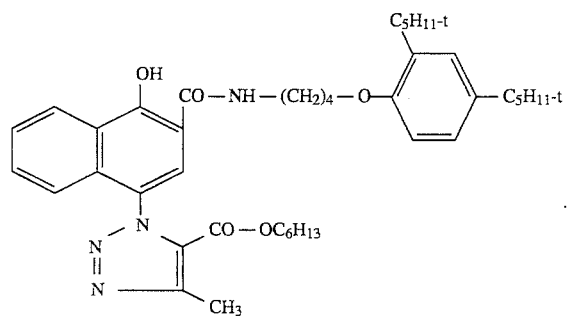

9. The compound of claim 2, wherein said compound has the formula

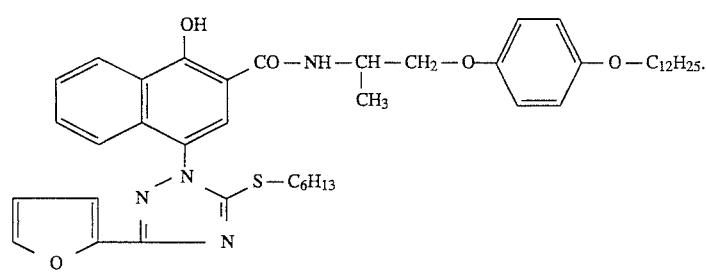

10. The compound of claim 2, wherein said compound has the formula

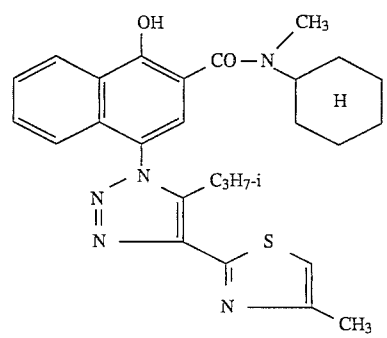

11. The compound of claim 2, wherein said compound has the formula

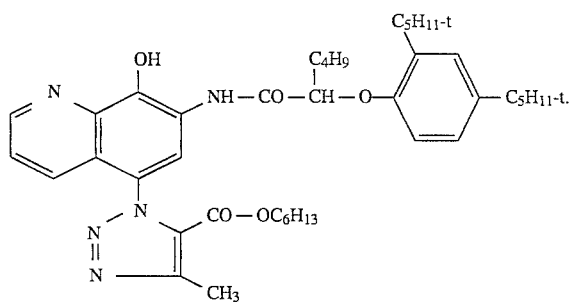

12. The compound of claim 2, wherein said compound has the formula

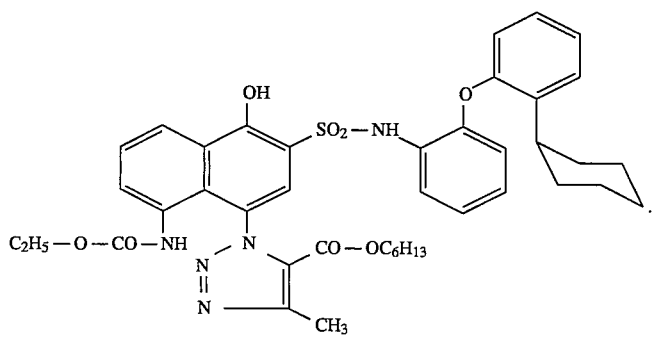
* * * * *

UNITED STATES PATENT AND TRADEMARK OFFICE
CERTIFICATE OF CORRECTION

PATENT NO. : 5,463,072
DATED : October 31, 1995
INVENTOR(S) : Peter Bergthaller

It is certified that error appears in the above-indentified patent and that said Letters Patent is hereby corrected as shown below:

On the title page, item [73]; "Agfa Gevart" should be --Agfa Gevaert--.

In claim 2 (column 11, line 58), insert --Q-- before the words "denotes a group for completing a condensed benzene or".

Signed and Sealed this

Second Day of July, 1996

*Attest:*

BRUCE LEHMAN

*Attesting Officer*  *Commissioner of Patents and Trademarks*